United States Patent [19]
Phillips et al.

[11] Patent Number: 4,852,200
[45] Date of Patent: Aug. 1, 1989

[54] DEVICE FOR CLEANING ELECTRIC KNIVES

[75] Inventors: James L. Phillips; Dale W. Richardson, both of Mattawan, Mich.; Lawrence M. Silverman, Danville, Calif.

[73] Assignee: Richardson & Associates, Ltd., Kalamazoo, Mich.

[21] Appl. No.: 157,289

[22] Filed: Feb. 17, 1988

[51] Int. Cl.$^4$ .............................................. A47L 25/00
[52] U.S. Cl. ................... 15/104 R; 15/236.09
[58] Field of Search ............... 15/236.09, 104 R, 142, 15/218.1; 211/69.8, 120; 206/0.8

[56] References Cited

U.S. PATENT DOCUMENTS 635,283  10/1899  Adair ................................. 211/69.8
982,795  1/1911  Cochran ............................ 211/69.8

Primary Examiner—Edward L. Roberts
Attorney, Agent, or Firm—Gordon W. Hueschen

[57] ABSTRACT

An electric-knife cleaning device useful in connection with surgery comprising a cleaning head mounted on a laminated base, the bottom lamina of which is a removable pull-off sheet adhered to said base by a tacky adhesive which remains on said base when said pull-off sheet is removed and is then operative to adhere said base to a surface, and the top lamina of which comprises means for mounting said cleaning head on said base, whereby the bottom lamina can be removed and the device adhered to a surface adjacent the situs of the surgery in a position convenient for cleaning the knife during the surgery, is disclosed, as well as a method for its production and use.

20 Claims, 1 Drawing Sheet

DEVICE FOR CLEANING ELECTRIC KNIVES

FIELD AND OBJECTS OF INVENTION

This invention relates to a device and method for cleaning electric knives used in surgery and is particularly directed to such a sterile device, a hermetically sealed package containing the same, and a method of making and of using the same.

Electric knives used in surgery have the disadvantage that cauterized flesh or skin tends to accumulate on the knife blade. Therefore, the blade must periodically be replaced or cleaned in place.

It is an object of the invention to provide a simple, effective, and economical device whereby such blades can be cleaned in place and which, moreover, enables the surgeon himself to do the cleaning quickly and effectively without having to call on a nurse or other attendant to clean the blade for him and to do so aseptically. It is a further object of the invention to provide a device of the class described which is economical to produce, easy to use, and effective for its intended purpose, as well as a method of making and using the same. Other objects of the invention will become apparent hereinafter and still others will be obvious to one skilled in the art.

SUMMARY OF THE INVENTION

The invention is primarily directed to an electric-knife cleaning device, preferably in sterile condition and/or in sterile hermetically-sealed packaging, which device comprises a cleaning head comprising a coil spring mounted on a laminated base, the bottom lamina of which is a removable pull-off sheet adhered to said base by a tacky adhesive which remains on said base when said pull-off sheet is removed and which is then operative to adhere said base to a table, bed-clothing, bed-linen, or like handy available surface, and the top lamina of which comprises means for mounting said cleaning head on said base whereby, when aseptically or sterilely packaged, the package can be opened, the bottom lamina removed, and the device adhered to a surface adjacent to the situs of the surgery in a position convenient for cleaning of the knife during the intended surgery.

The invention also includes one or more further features in which the cleaning head comprises a tightly-wound coil spring in which the convolutions of the coil are juxtaposed whereby, when the blade of the knife is drawn through the juxtaposed convolutions, it will be wiped clean; in which the last convolution at each end of the coil comprises a leg portion which extends tangentially from the last convolution, preferably in a direction substantially normal to said base, each of which leg portions has its end bent to form two feet, one on each leg, said feet being anchored between said top lamina and the next adjacent lamina; in which said leg portions before being anchored to said base are at an angle to each other such that when they are brought to their ultimate and preferably parallel position and anchored to said base, the spring is under tension; in which the top lamina comprises a relatively thin, flat, non-tacky, flexible and resilient plastic sheet having apertures therein in a position adapted to receive the legs of said spring and to hold them, preferably in substantially vertical positions, generally parallel one to the other and normal to said base, and wherein the lamina adjacent to the top lamina comprises soft plastic material, said top flat plastic sheet being sufficiently flexible that it can be bent so that said feet can be inserted through said apertures and be embedded in said soft plastic material at the interface between said plastic sheet and the juxtaposed lamina of soft plastic material, and said plastic sheet being sufficiently resilient that it will return to a flat condition after having been bent; in which said feet are bent away from each other, preferably at a right angle to their respective legs, whereby the spring tension aids in inserting the feet through said apertures when the flat plastic sheet is bent; and in which the soft plastic material is a plastic or elastomeric foam, preferably polyethylene foam or the like.

The invention also relates to a cleaning device for the blades of electric knives which device comprises one or more of the various features stated in the foregoing.

The invention, moreover, also relates to a method for assembling such a cleaning device having a laminated base comprising a relatively thin, non-tacky, flat, flexible and resilient plastic sheet adhered to an underlying, preferably thicker, sheet of soft plastic material which has a tacky surface covered by a removable pull-off sheet and a cleaning head comprised of a coil spring having legs at each end which extend at an angle from the end convolutions of the coil spring and have portions at the end thereof bent out at angles, preferably right angles, to said legs, forming apertures in said plastic sheet in position such that, if said legs were in them, they would be substantially parallel to each other and preferably normal to said base, inserting the end of one foot into the aperture intended for its leg, rotating the other leg to place the spring under tension and to bring the end of its foot into alignment with the other aperture, bending said base on a centerline between said apertures sufficiently to admit said last-named foot and inserting that foot into that aperture either by extraneous force or by the force engendered by the tension on the coil spring or both.

The invention also relates to a method for performing surgery with an electric knife which comprises the step of cleaning the blade of the knife by drawing it between the convolutions of a coil spring in which the convolutions thereof are juxtaposed and preferably in which the coil spring is mounted on an adhesive-backed base having a removable pull-off sheet and in which the method includes the steps of pulling off of said removable sheet and adhering the adhesive-backed base to a surface in proximity to the situs of the surgery and convenient to the surgeon while performing surgery with the electric knife.

The invention in its broadest aspects comprises a cleaning device for the blade of an electric knife which device comprises a base member comprising a first sheet adhered to an underlying sheet and a cleaning head comprising a coil spring having a leg at each end which extends through apertures in said first sheet and terminates in a foot anchored at the interface between said first sheet and said underlying sheet, and such device wherein said base is provided with securement means for securement thereof to a surface to which it is desired to be attached, as well as such devices in sterile condition and especially in sterile condition hermetically sealed in a package therefor.

DETAILED DESCRIPTION OF A PREFERRED EMBODIMENT

Figure 1:
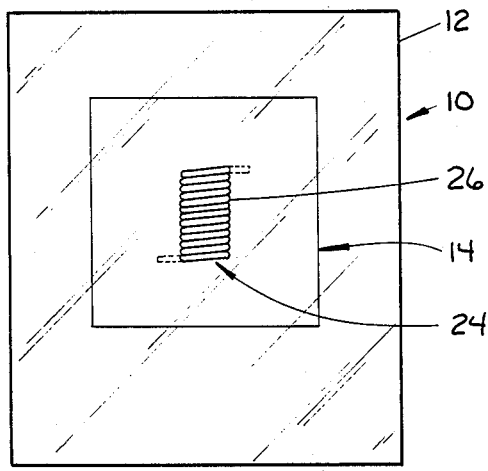
FIG. 1 is a plan view of a package according to the invention.
Figure 4:
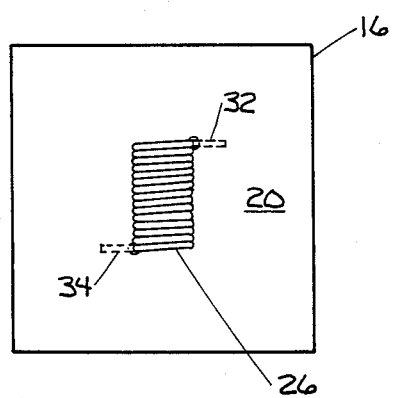
FIG. 4 is a plan view of a device according to the invention.
Figure 6:
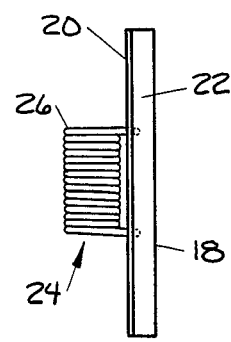
FIG. 6 is a side view of FIG. 4.
Figure 8:
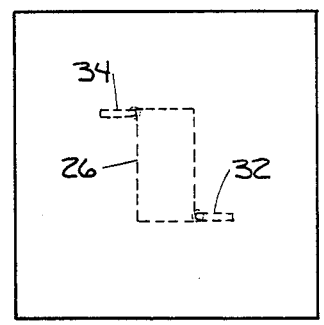
FIG. 8 is a bottom view of FIG. 4.

FIG. 1 shows a hermetically sealed package 10 according to the invention in which 12 is an envelope preferably having at least one transparent face. Inside the envelope 12 is a cleaning device 14 according to the invention comprising cleaning head 24 consisting essentially of coil spring 26 mounted on base 16 (FIG. 4).

The cleaning device 14 has a laminated base 16 comprising a central layer or lamina 22, a top lamina 20, and a bottom lamina which is a thin removable pull-off sheet 18 so thin that it is illustrated by a line. The top lamina 20 is a relatively thin, flat, non-tacky, flexible and resilient plastic sheet 20, which is adhered to a sheet of soft plastic material 22 substantially thicker than the top plastic sheet 20. In a less advantageous embodiment, top lamina 20 may be of resin-impregnated or coated or heavily clay-coated cardboard or paperboard or other hard-surface sterilizable material or like sheet material which is water impermeable and preferably also water insoluble. The bottom of central lamina 22 is covered by a removable pull-off sheet 18 which, when removed, leaves a tacky surface at the bottom of base 16 for adherence to a convenient adjacent surface.

Advantageously, the soft plastic material 22 comprises a relatively soft plastic or elastomeric foam such as polyurethane, polystyrene, and preferably polyethylene foam, about one-eighth of an inch thick. It is to be understood, however, that this as well as any other dimensions are given by way of illustration only and that the invention is not limited to the particular dimensions given or, for that matter, to any particular material, as long as the base 16 and components thereof have the requisite characteristics to function in the manner herein described.

The top lamina or layer 20 advantageously is a flat sheet or board, preferably of plastic, which is usually thin relative to the underlying relatively soft material 22 is non-tacky or at least has a non-tacky upper surface, is flexible and resilient, and preferably white (indicative of sterility). Various plastics, such as polyalkylenes, polycarbonates, nylon, polyesters, polyacrylates, polyurethanes and the like, can be used. It may have a thickness on the order of about 0.02 inch and advantageously approximately one-sixth the thickness of the softer plastic material 22.

There are available on the market plastic foam sheets having adhesive on both sides and removable pull-off sheets, usually of thin paper or plastic, for protecting the adhesive until use. One such material is marketed by Minnesota Mining and Manufacturing Company (3M) as 3M 1511 double-backed tape. It comprises polyethylene foam as its central layer. Other equivalent double-backed tape comprising other plastic foams, for example a polystyrene or other plastic foam or a polyurethane or other elastomeric foam can be used. In employing such double-backed foams, the top pull-off sheet is pulled off and replaced by the plastic sheet 20.

Figures 2, 3:
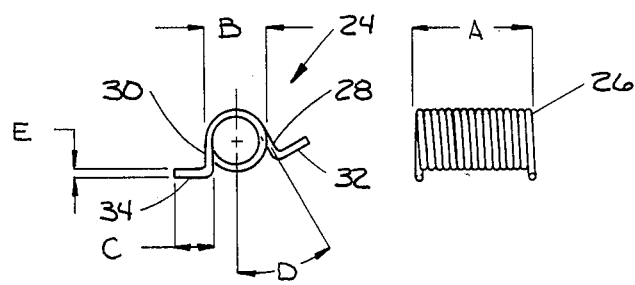
FIG. 2 is a side view of a cleaning head according to the invention.
FIG. 3 is an end view of FIG. 2.

The cleaning head 24 is fastened in the approximate center of base 16. It comprises a coil spring 26 of stainless steel or chrome-plated piano wire, or of other non-corrosive wire. Suitably it comprises about 18–20 coils of wire of about 0.04 inch in diameter and may be about three-fourths (¾) of an inch long (A) and have a diameter (B) of about one-half its length. The end convolutions are extended tangentially at an angle D to each other to form divergent legs 28 and 30. The angle D suitably is about 30 degrees. The legs 28 and 30 have their ends bent out at an approximately right angle as shown in FIG. 3 to form diverging feet 32 and 34. These feet have a diameter E of about 0.04 inch which normally is the same as or approximately the same as that of the wire.

Figure 7:
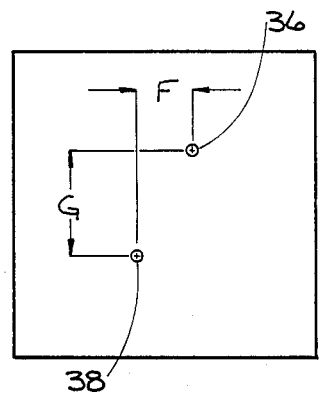
FIG. 7 is a plan view of a base member of FIG. 4 without the cleaning head thereon.

The sheet or board 20 has two apertures 36 and 38 therein as shown in FIG. 7. These apertures advantageously have a diameter somewhat larger than the diameter of the wire, say, from 50% to 100% greater. They are located on the sheet 20 so that the distance F is substantially the same as the diameter of the coil spring 26 and the distance G is substantially the same as the length of the coil spring 26.

The device is assembled by inserting the foot 34 in aperture 38 and then rotating the leg 28 clockwise until the end of its foot 32 can be inserted in aperture 36. To facilitate this the flat sheet 20 advantageously is bent or flexed along its vertical centerline as needed to bring the foot 32 to a point where it can be inserted into aperture 36. Since the coil spring 26 has been placed under tension by the clockwise rotation of the leg 28, this tension may be sufficient to force the foot 32 into place in aperture 36. In any event, the residual tension tends to force the legs apart against the outside of the apertures 36 and 38 and thus provides a rigid mounting for the cleaning head 26 even when the apertures are somewhat larger than the diameter of the feet. The relatively soft plastic material 22 is laminated on the plastic sheet 20 and, being softer, the feet 32 and 34 become embedded in it. If desired, the soft plastic material 28 can be laminated to sheet 20 before the feet are inserted in sheet 20, in which case care should be taken to bend or flex sheet 20 sufficiently so that the feet can be inserted therein and located along the interface between the underlying soft plastic material 22 and the upper plastic sheet 20. Although the foregoing illustrates the preferred manner of assembly, an alternative manner which is especially suitable when the top sheet is extremely stiff or thick, involves inserting the legs through the apertures and then fashioning the feet on the ends thereof while said legs are on the underside of said top sheet, thereby securing the same in said apertures.

Figure 5:
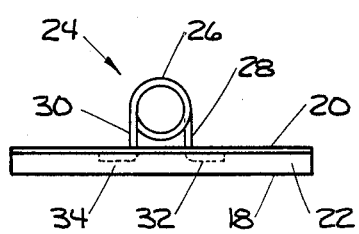
FIG. 5 is an end view of FIG. 4.

The feet 32 and 34 have a length D sufficient to keep the legs 28 and 30 from being withdrawn, but advantageously are considerably longer, as shown in FIGS. 3 and 5, in order to provide greater contact with the underlying layer, e.g., the relatively soft plastic material layer 22. Suitably, they may be as long as about one-fourth (¼) of an inch or so.

There is thus provided a device for cleaning the blades of electric knives which can be sterilized and aseptically packaged and then, at the time of use, aseptically removed from the package by the surgeon or his assistant and aseptically mounted, by first removing the removable pull-off sheet, and then adhering the device to a convenient surface which may be bed-clothes, bed-linen, a table, or like convenient surface where the cleaning head will be readily available to the surgeon whenever the knife blade requires cleaning. Once the device is mounted, the surgeon need only turn off the electricity and wipe the knife blade clean by drawing it between the closely juxtaposed convolutions of the cleaning head coil spring. The device is expendable because of its low cost and may be disposed of at the end of each surgery or replaced, whenever a fresh or completely sterile device is desired, by another new device of the same type.

Although the invention has been described with reference to a preferred embodiment, it is to be understood that it is not limited thereto as many variations which are within the scope of the invention will occur to those skilled in the art once they are aware of this disclosure.

We claim:

1. An electric-knife cleaning device useful in connection with surgery which device comprises a cleaning head mounted on a laminated base, the bottom lamina of which is a removable pull-off sheet adhered to said base by a tacky adhesive which remains on said base when said pull-off sheet is removed and is then operative to adhere said base to a surface, and the top lamina of which comprises means for mounting said cleaning head on said base, whereby the bottom lamina can be removed and the device adhered to a surface adjacent the situs of the surgery in a position convenient for cleaning the knife during the surgery, in which the cleaning head comprises a tightly-wound coil spring in which the convolutions of the coil are juxtaposed whereby, when the blade of the knife is drawn through juxtaposed convolutions, it will be wiped clean, and in which the last convolution at each end of said spring has s leg portion which extends tangentially from the last convolution, both of which leg portions have their ends bent to form two feet, one on each leg, said feet being anchored between said top lamina and an under-lying lamina.

2. A device of claim 1 in which said leg portions extend from the last convolutions in a direction substantially normal to said base and said leg portions, before being anchored to said base, are at an angle to each other such that, when they are brought to a parallel position and anchored to said base, the spring is under tension.

3. A device of claim 2 in which the top lamina comprises a relatively thin, flat, non-tacky, flexible and resilient plastic sheet having apertures therein in a position to receive the legs of said spring and hold them in substantially vertical positions parallel one to the other and substantially normal to said base, and the lamina underlying the top lamina is of soft plastic material, said flat plastic sheet being sufficiently flexible so that it can be bent to permit said feet to be inserted through said apertures and become embedded in said underlying soft plastic material and sufficiently resilient that it will return to a flat condition after having been so bent.

4. A device of claim 3 in which said feet are bent away from each other at a substantially right angle to their respective legs whereby the spring tension aids in inserting said feet through said apertures.

5. A device of claim 4 in which the soft plastic material is a plastic or elastomeric foam.

6. A device of claim 1 in which said base has a central lamina which comprises a soft plastic material having tacky adhesive on each face, the top face of which is laminated to a top lamina comprising a relatively thin, hard flat, non-tacky, flexible and resilient plastic sheet and the bottom face of which is laminated to the bottom lamina comprising a removable pull-off sheet.

7. A device of claim 6 in which the soft plastic material is polypropylene foam.

8. A device of claim 6 in which the feet are embedded at the interface between said top lamina and said underlying central lamina of soft plastic material.

9. The device of claim 1 in sterile condition and ready for use.

10. The device of claim 1 in sterile condition hermetically sealed in a package therefor and ready for use.

11. A cleaning device for the blade of an electric knife which device comprises a base member comprising a relatively thin, flat, non-tacky, flexible and resilient sheet adhered to an underlying thicker sheet of relatively soft material which has a tacky surface covered by a removable pull-off sheet and a cleaning head comprising a coil spring having a leg at each end which extends through apertures in said sheet and terminates in a foot anchored at the interface between said sheet and said underlying relatively soft material.

12. A cleaning device of claim 11 in which the coil spring is under tension for causing the legs to spring out and anchor securely in the base member.

13. A cleaning device of claim 12 in which the relatively soft material is a plastic or elastomeric foam and said sheet is a plastic sheet.

14. A cleaning device of claim 12 in which said feet are portions of said legs bent in opposite direction at substantially right angles to said legs.

15. A cleaning device of claim 14 in which said sheet is sufficiently flexible so that it can be bent to permit the ends of said feet to enter said apertures and sufficiently resilient so that it can resume its original flat condition after being so bent.

16. The device of claim 11 in sterile condition and ready for use.

17. The device of claim 11 in sterile condition hermetically sealed in a package therefor and ready for use.

18. A cleaning device for the blade of an electric knife which device comprises a base member comprising a first sheet adhered to an underlying sheet and a cleaning head comprising a coil spring having a leg at each end which extends through apertures in said first sheet and terminates in a foot anchored at the interface between said first sheet and said underlying sheet, wherein said base is provided with securement means for securement thereof to a surface to which it is desired to be attached in the form of a contact adhesive on the lower surface of said underlying sheet and a removeable cover sheet for said contact adhesive.

19. The device of claim 18 in sterile condition and ready for use.

20. The device of claim 18 in sterile condition hermetically sealed in a package therefor and ready for use.

* * * * *

UNITED STATES PATENT AND TRADEMARK OFFICE
CERTIFICATE OF CORRECTION

PATENT NO. : 4,852,200

DATED : August 1, 1989

INVENTOR(S) : James L. Phillips, Dale W. Richardson and Lawrence M. Silverman

It is certified that error appears in the above-identified patent and that said Letters Patent is hereby corrected as shown below:

Col. 5, line 39; "has s leg" should read -- has a leg --

Signed and Sealed this

Twenty-first Day of August, 1990

Attest:

HARRY F. MANBECK, JR.

Attesting Officer

Commissioner of Patents and Trademarks